(12) United States Patent
Habermeyer

(10) Patent No.: US 10,478,308 B2
(45) Date of Patent: Nov. 19, 2019

(54) ELLIPSOIDALLY-SHAPED HUMERUS HEAD PROSTHESIS

(71) Applicant: Peter Habermeyer, München (DE)

(72) Inventor: Peter Habermeyer, München (DE)

(\*) Notice: Subject to any disclaimer, the term of this patent is extended or adjusted under 35 U.S.C. 154(b) by 0 days.

(21) Appl. No.: 16/210,373

(22) Filed: Dec. 5, 2018

(65) Prior Publication Data

US 2019/0105168 A1 Apr. 11, 2019

Related U.S. Application Data

(63) Continuation of application No. PCT/EP2017/063491, filed on Jun. 2, 2017.

(30) Foreign Application Priority Data

Jun. 6, 2016 (EP) .................................... 16173142

(51) Int. Cl.
*A61F 2/40* (2006.01)
*A61F 2/30* (2006.01)

(52) U.S. Cl.
CPC .. *A61F 2/4014* (2013.01); *A61F 2002/30253* (2013.01); *A61F 2002/30332* (2013.01); *A61F 2002/4018* (2013.01); *A61F 2002/4037* (2013.01)

(58) Field of Classification Search
CPC ............. A61F 2/40; A61F 2/28; A61F 2/4014
See application file for complete search history.

(56) References Cited

U.S. PATENT DOCUMENTS

| 4,550,450 | A | 11/1985 | Kinnett |
| 7,648,530 | B2* | 1/2010 | Habermeyer ......... A61F 2/4003 623/19.11 |
| 2006/0009852 | A1 | 1/2006 | Winslow et al. |
| 2007/0225818 | A1 | 9/2007 | Reubelt et al. |
| 2007/0282450 | A1* | 12/2007 | Habermeyer ......... A61F 2/4003 623/19.14 |
| 2011/0054624 | A1* | 3/2011 | Iannotti .................. C12N 15/86 623/19.14 |
| 2012/0232668 | A1 | 9/2012 | Iannotti |
| 2015/0250601 | A1 | 9/2015 | Humphrey |

FOREIGN PATENT DOCUMENTS

DE 102004042502 A1 3/2006

\* cited by examiner

*Primary Examiner* — Jason-Dennis N Stewart
(74) *Attorney, Agent, or Firm* — Quarles & Brady LLP; Yakov S. Sidorin

(57) ABSTRACT

A humerus head implant includes a head cap, a fixing component, and a bone-screw component. The head cap has a shape of half-an-ellipsoid extending into a positive z-direction along the z-axis, in positive and negative x-directions, and in positive and negative y-directions. The extension along the x-direction is in a range of 0.8 to 0.95 of the extension in the y-direction. There is a conical recess having a center axis that is displaced in the negative y-direction with respect to the z-axis and configured to interface with a conical section of the fixing component. This allows for rotation of the head cap relative to the fixing component.

11 Claims, 8 Drawing Sheets

ELLIPSOIDALLY-SHAPED HUMERUS HEAD PROSTHESIS

CROSS-REFERENCE TO RELATED APPLICATIONS

This application is a continuation of the pending International Application No. PCT/EP2017/063491 filed on 2 Jun. 2017, which designates the United States and claims priority from the European Application No. 16173142.7 filed on 6 Jun. 2016. The disclosure of each of the above-identified applications is incorporated herein by reference.

BACKGROUND

1. Field of the Invention

The invention relates to a prosthesis to a shoulder joint prosthesis and, in particular, to a humerus implant.

2. Description of Relevant Art

The shoulder joint is a ball-and-socket-joint. It has an exceptional range of motion. The shoulder joint may be replaced or repaired if it suffers from instability or other maladies, such as arthrosis or fracture.

A humerus prosthesis is disclosed in US 2011/0320004 A1. The prosthesis has a shaft which in operation is anchored into the humerus. The shaft holds a head which has a spherical cap.

WO 2005/070345 A1 discloses a shoulder joint prosthesis with a spherical cap attached to an anchoring section which, in operation, is directly anchored into the bone of a humerus head. It does not require an elongated shaft anchored in the humerus. This design allows for a simple, cement-free anchoring with excellent mechanical properties. The disadvantage manifests in a higher wear of the articular cartilage of the glenoid. Literature reports a glenoid wear in 25% of patients after 4 years from receiving hemiarthroplasty.

US 2007/225818 A1 discloses non-spheric articulating surfaces in shoulder and hip replacement having a free shape and not any geometric curvature.

US 2012/232668 discloses a shoulder joint with a variable offset mounting.

SUMMARY

The embodiments provide a humeral head prosthesis which, in practice, can easily be implanted into the bone of the humerus and which provides a reduced wear of the articular cartilage of the glenoid. Furthermore, the implantor implant component is characterized by high mechanical stability, a long lifetime, and comparatively low manufacturing costs.

In a first embodiment, the prosthesis includes a head cap and a fixing component configured to fix the head cap to the humerus head. The articulating surface of the head cap has the shape of a half of an ellipsoid and, preferably, of a half of a three-axis ellipsoid. The head cap preferably has a conical recess dimensioned to match a conical section of the fixing component. This conical section of the fixing component preferably is attached to a holding device, preferably a bone screw that in practice allows to anchor the fixing component in the bone material of a humerus head without requiring a shank anchored in the humerus shaft.

The half-ellipsoidally-shaped prosthesis head (that is, the prosthesis head dimensioned as half of an ellipsoid, having a body configured as half-ellipsoid) extends into the directions of an x-axis, a y-axis, and a z-axis. In practice, the z-axis is oriented towards the glenoid of a shoulder, while the x-axis is oriented in an anterior-posterior (transversal plane) direction. The y-axis is oriented craniocaudally (frontal plane) direction. The extension of the head cap is largest along the y-axis. In the direction of the x-axis, there is a smaller extension that is in a range of about 0.8 to about 0.95 of the extension in the y-axis. Most preferably, this ratio is between 0.85 and 0.95. A further preferred range is between 0.90 and 0.91. The extension of the head-cap in the direction of the z-axis is the smallest, and is preferably below 50 percent of the extension in the y-direction. The head cap has the shape of half of an ellipsoid (and is interchangeably referred to as an ellipsoidal head, for short), as in the chosen system of coordinates there is only an extension into positive z-direction, but no extension in a negative z-direction. The head cap may have an extension in the z-direction in a range between 30% to 40% of the extension in the y-direction or between 32% to 38% of the extension in the y-direction. Preferably, the angle between the articulating surface and the extension surface or the bottom surface of the implant component is less than 90 degrees. Such angle is preferably between 60 and 80 degrees, and most preferably between 62 and 70 degrees.

Furthermore, a center axis defined by the conical recess in the head cap has an offset with respect to the z-axis of the half-ellipsoid. Most preferably, the center of the conical recess is offset or displaced to be below the z-axis (or offset in a negative y-direction relative to the z-axis) of the half-ellipsoidal head cap. The value of such displacement preferably is in a range between about 3 and about 10 mm, and most preferably is in a range between 4 and 6 mm.

Such configuration of the implant component leads to multiple advantages over the prior art. Due to the ellipsoidal shape, the contact area with a glenoid is significantly enlarged, as evidenced by a large number of measurements with statistical evaluation conducted at human shoulder joints. Due to the enlarged contact surface, the surface pressure imposed by the implant is lowered, in comparison with implants of related art, thereby decreasing the wear of the cartilage and the wear of the prosthesis head cap. The reduction of wear, in turn, increases lifetime of the prosthesis and increases time-intervals at which the condition of the shoulder should be revised or assessed. The offset between the center of the conical recess and the z-axis of the head cap allows, in practice, for an easy adaption of the ellipsoidally-shaped head cap to the actual shape of the humerus during the process of implantation of the prosthesis. A further benefit is provided by the displacement of the position of the bone screw component within the humerus head towards the humerus, which results in improvement of the quality of anchoring due to the availability of more bone material with which the bone screw component is spatially coordinated and due to a shorter path through which the articulate forces have to be guided towards the humerus bone.

Preferably, the implant further includes a head adapter and a bone screw component. Generally, the bone screw component may be configured as any means for screwing or holding a piece into the humerus bone material. It is preferred if the bone screw component contains a plurality of holes to allow for bone ingrowth after the implantation has been accomplished. The head adapter and/or the bone screw component may also be configured as one single part, or they may include additional (sub-)components. In one embodiment, the bone screw component has at least one thread to be screwed directly into the humerus bone. The bone screw component preferably includes a centering shaft and a limit stop. The head adapter preferably has at least one protrusion, which in practice may be pressed into the bone material of the humerus to secure the implant from being rotated or against rotating. Therefore, the head adapter is secured against rotation independently from the screw. Such configuration allows, during implantation, for rotation of the screw while the head adapter does not rotate. Most preferably, the head adapter contains between 2 and 10 protrusions. The head adapter furthermore preferably has a center bore, which further preferably has a chamfered bottom section. It is preferred, in one embodiment, if the center bore is adapted to the centering shaft of the bone screw component, and the chamfer is adapted to fit to the limit stop of the bone screw component. Such configuration allows for precise positioning and fixing of the bone screw component to the head adapter. It is further preferred if the head adapter has a head contact surface, which may have a rim. In practice, this head contact surface may be used for optimized load transfer from the head cap via the head adapter into the bone. Furthermore, it is preferred if the head adapter provides a conical section preferably dimensioned to fit into the conical recess of the ellipsoidal head.

A further embodiment relates to a method for implanting or installing a humerus head implant. In a first step, the original head of the humerus is resected. In a second step, a stud hole is made or formed in the resected humerus head surface, preferably by a drill or by a reamer. In a third step, a head cap holder, which may be a fixing component comprising a bone screw or any other holding device, is implanted or installed into or cooperated with the humerus head bone. Preferably, the fixing component comprises a conical section fitting to a conical recess in a humerus head cap. A fourth step includes the process of attachment of a humerus head cap having a half-ellipsoidal shape as mentioned above, and a conical recess having a center axis offset to the z-axis of the ellipsoid. A fifth step includes rotating the half-ellipsoidal head cap into a position in which the cap fits to the bone of the humerus head and/or to the glenoid. This latter step is optional, as the head cap may have been attached in the correct position and/or direction during the previous step.

BRIEF DESCRIPTION OF THE DRAWINGS

In the following description, the idea of the invention is described without limitation of the general inventive concept with reference to examples of embodiments and to the drawings.

Figure 1:
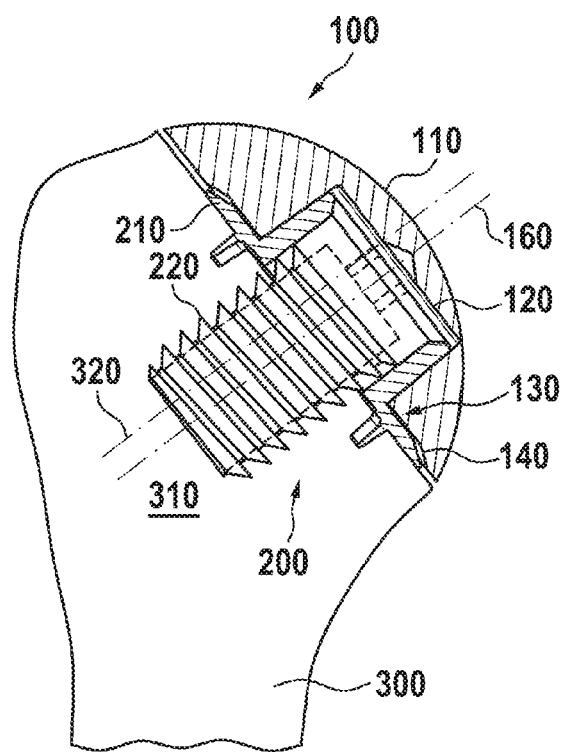
FIG. 1 shows a humerus head with an embodiment of the implant.

While the invention may be implemented in variously-modified ways and assume alternative forms, specific embodiments of the invention are shown by way of example in the drawings and will herein be described in detail. It should be understood that the drawings and detailed description are not intended to limit the invention to any particular form disclosed, but to the contrary, the scope of the invention is intended to cover all modifications, equivalents and alternatives as defined by the appended claims.

DETAILED DESCRIPTION

In FIG. 1, a humerus head with a humerus head implant is shown. The humerus 300 has a humerus head 310 bearing a head cap 100 by means of a fixing component 200. The head cap 100 includes an articulating surface 110, which is designed to fit to a glenoid, in practice. Opposing to the articulating surface 110 is a conical recess 120 adapted to hold the fixing component 200. There may also be an adapter contact surface 130 opposite to the articulating surface for load bearing, and therefore configured to transfer mechanical load from the head cap 100 into the fixing component 200. There may further be a rim 140 at the outside of the adapter contact surface 130. The fixing component may have a threaded bone screw component 220 dimensioned to anchor the implant into the bone material of the humerus head 310.

FIG. 1 further shows the center axis 160 of the conical recess, which preferably is also the center axis of the fixing component 200 and/or preferably the center axis of the bone screw component 220. This center axis of the conical recess preferably is offset from or displaced with respect to the humerus center 320, in a direction towards the shaft of the humerus to ensure an improved load transfer and improve embedding of the implant into the humerus bone material. Preferably, the center is related to the resected bone area configured to place the implant.

Figure 2:
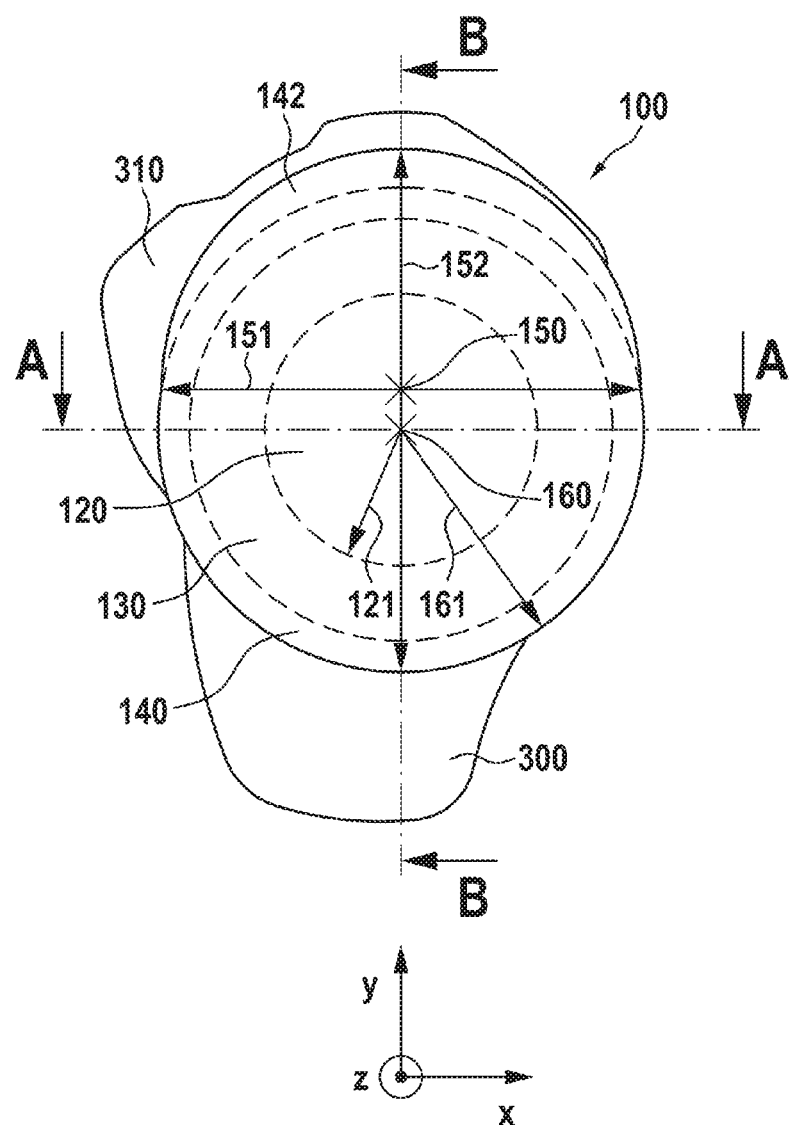
FIG. 2 illustrates a front view of a portion of the embodiment of the implant on a humerus.

In FIG. 2, a front view of the implant is shown disposed on a humerus. The head cap 100 is located on the humerus head 310. For a better orientation, a coordinate system is shown. It has a z-axis extending out of the drawing plane, an x-axis pointing to the right, and a y-axis pointing to the top of FIG. 2. The center of the coordinate system is at the center 150 of the ellipsoidally-shaped head cap. The ellipsoidally-shaped head cap has an extent 151 in the x-direction (head cap width) and an extent 152 in y-direction (head cap height), whereas the head cap height is larger than the head cap width. The conical recess 120, which is shown here with a dashed line because it is hidden from view within the head cap, has a radius 121, whereas the outer radius of the rim of adapter contact surface 140 has a radius 161. The center 160 of the conical recess is offset to the bottom or in a negative y-direction from the center 150 of the ellipsoid head. Actually, the ellipsoidal head cap is configured only as half-an-ellipsoid, which will be shown later in detail.

Figure 3:
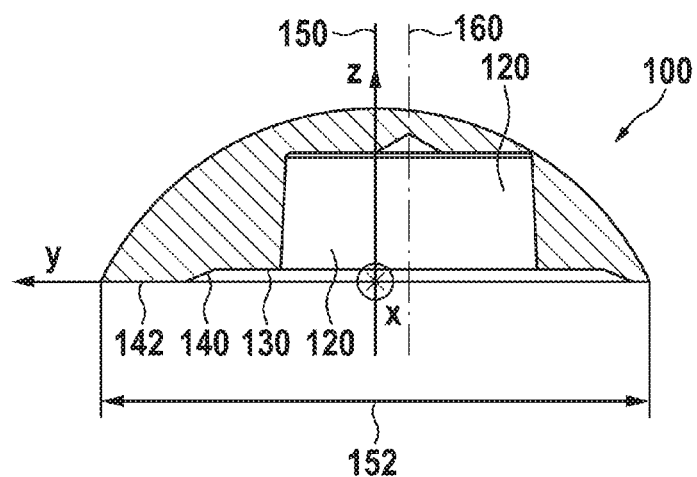
FIG. 3 depicts a sectional view of the portion of the embodiment of the implant along the y-axis.

In FIG. 3, a sectional view along the y-axis (section B-B of FIG. 2) is shown. Here, the larger diameter 152 (head cap height) is shown from left to right. There is an extension surface 142 at the bottom of the head cap, corresponding to the additional area caused by the larger head cap height as compared to the head cap width. Furthermore, the displacement of the center 160 of the conical recess against the z-axis 150 of the ellipsoidal head is shown. FIG. 3 clearly illustrates that the ellipsoidal-shape of the head cap only extends into a positive z-direction and has no negative z-dimension, in the chosen system of coordinates. Therefore, the shape of the head cap is only a half-ellipsoidal-shape.

Figure 4:
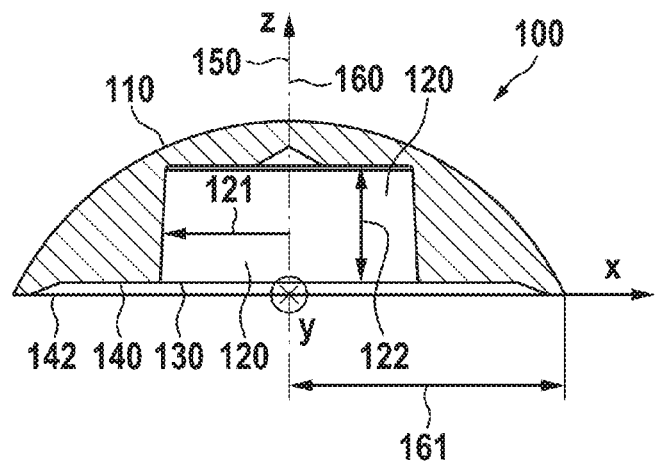
FIG. 4 presents a sectional view of the portion of the embodiment of the implant along the x-axis.

In FIG. 4, a sectional view along the x-axis (section A-A of FIG. 2) is shown. In this view, the center 160 of the conical recess 120 and the z-axis of the ellipsoidal head z are behind each other and overlap or coincide in the view of FIG. 4. FIG. 4 additionally illustrates the dimensions of the conical recess 120, which include a recess height 122 and a recess radius 121. As the recess 120 has a conical shape, the radius 121 is decreasing with the increasing zcoordinate. Accordingly, the radius 121 is largest at the bottom of the head cap (at z=0), and is decreasing with the height of the ellipsoidally-shaped head cap.

Figure 5:
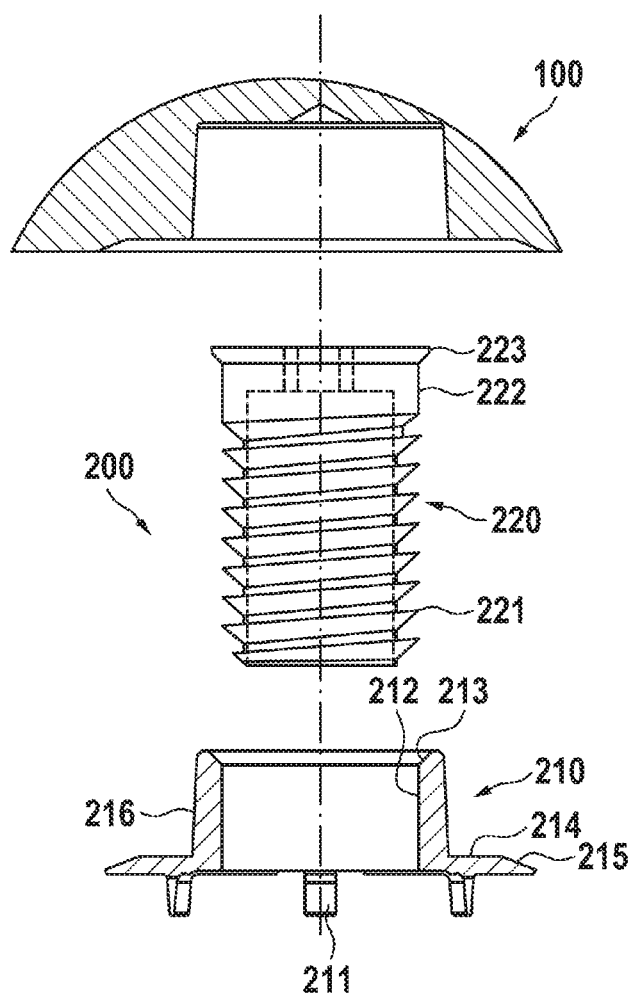
FIG. 5 exhibits components of the embodiment of the implant.

In FIG. 5, the components of the overall implant are shown side by side. These components include a half-ellipsoidal head cap 100 and a fixing component 200, which further includes a head adapter 210 and a bone screw component 220. Generally, the bone screw component 220 may include any means configured secure the overall implant (for example, to screw or hold) at the humerus bone material. The head adapter 210 and the bone screw component 220 may also be of one part or they may include further components. As shown, the bone screw component has at least one thread 221 and is dinnensioned to be screwed directly into the humerus bone. The bone screw component preferably includes a centering shaft 222 and a limit stop 223. The head adapter 210 preferably has at least one protrusion 211, which in practice may be pressed into the bone material of the humerus to secure the implant against a rotational motion. The head adapter 210 furthermore preferably has a center bore 212, which further preferably has a chamfered bottom section 213. It is preferred, if the center bore 212 is adapted to the centering shaft 222 of the bone screw component, and the chamfer 213 is adapted to fit to the limit stop 223 of the bone screw component. Such configuration allows for a precise positioning and fixing of the bone screw component to the head adapter. It is further preferred, if the head adapter has a head contact surface 214, which in turn may have a rim 215. This head contact surface 214 may be used, in practice, for optimized load transfer from the head cap 100 via the head adapter into the bone. Furthermore, it is preferred if the head adapter 210 provides a conical section 216 preferably dimensioned to fit into the conical recess 120 of the ellipsoid head.

Figure 6:
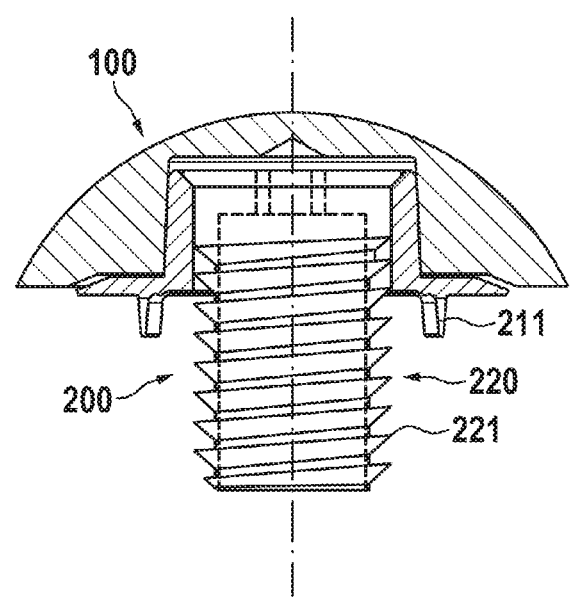
FIG. 6 portrays a fully assembled embodiment of the implant.

In FIG. 6, a fully assembled implant comprising the components as shown in the previous FIG. 5 is shown.

Figure 7:
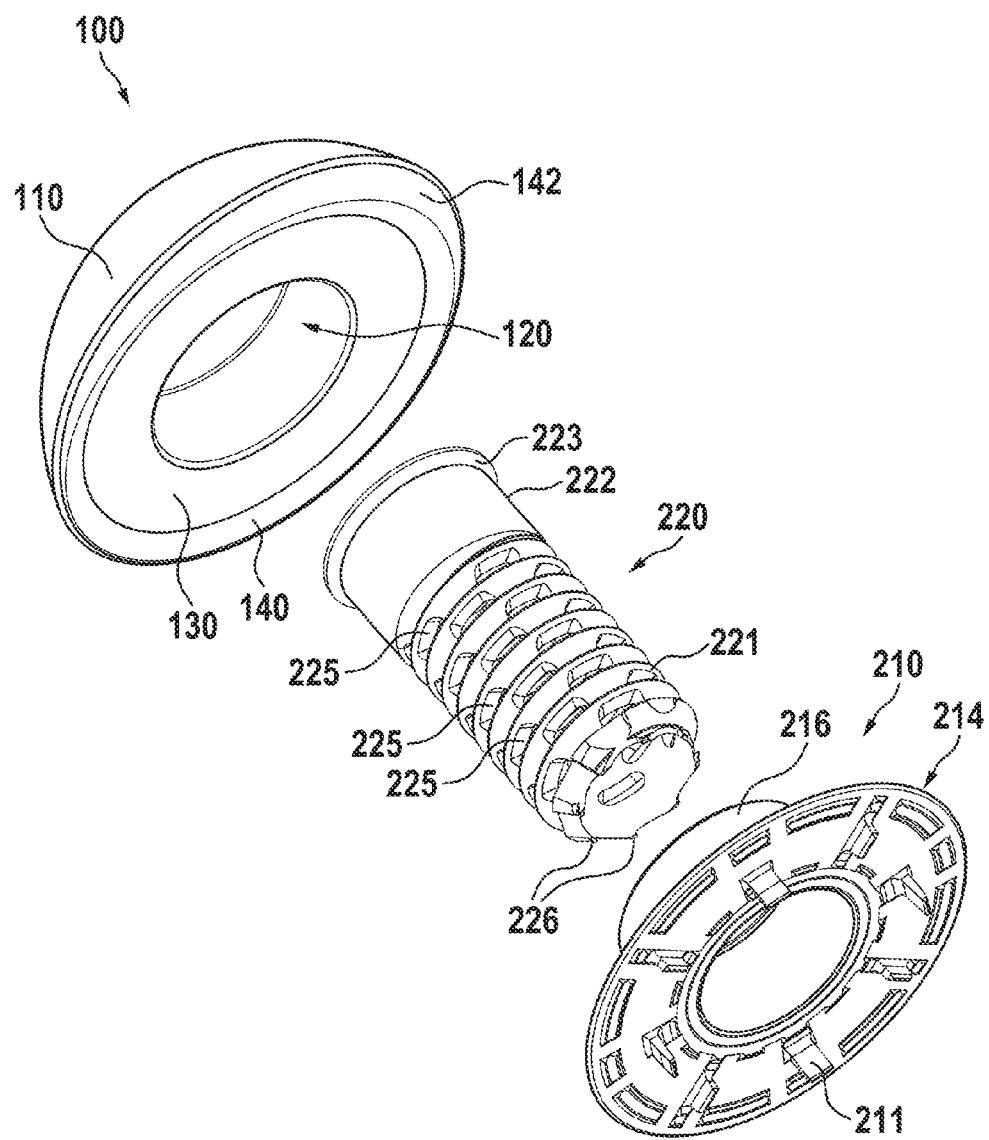
FIG. 7 reveals the components of the embodiment of the implant in a perspective exploded view.

In FIG. 7, the components of the embodiment of the overall implant are shown in a perspective view. In this FIG. 7, a modified embodiment with the bone screw component 220 that has a plurality of holes 225. Equipping the screw component 220 with a plurality of holes allows and facilitates, in practice, ingrowth of the bone into the screw component and therefore improves anchoring of the implant in the bone material. Furthermore, there exist cutting edges 226 at the end of the thread 221, which simplify the screwing of the screw component into (the attachment of the screw component to) the bone material.

Figure 8:
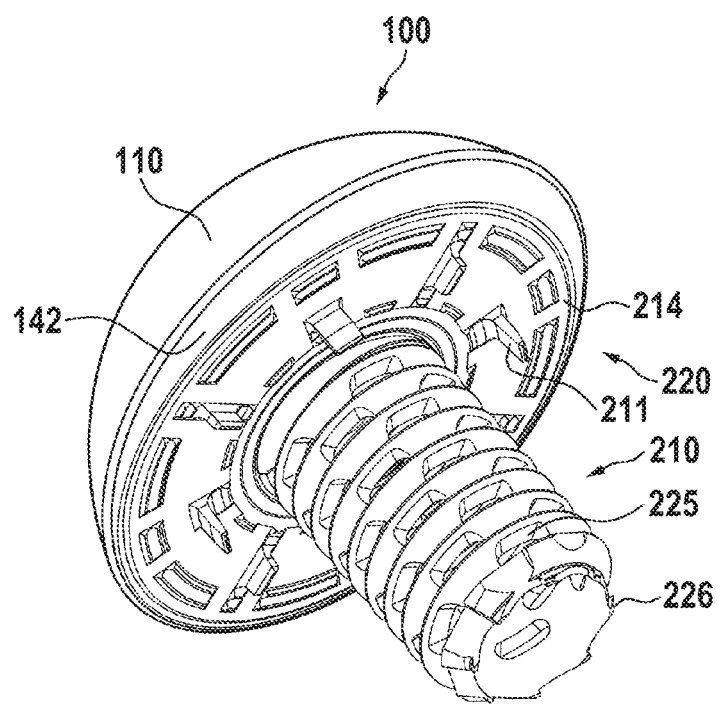
FIG. 8 shows the embodiment of the fully assembled implant in a perspective view.

In FIG. 8, an embodiments of the fully assembled implant is shown in a perspective view.

Figure 9:
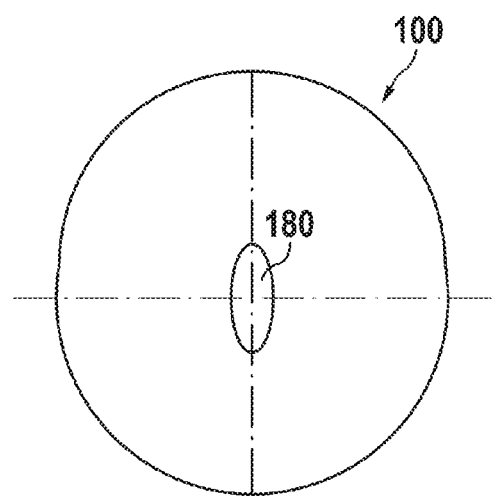
FIG. 9 shows the contact surface of the ellipsoidal head cap configured to contact a glenoid of the shoulder.

In FIG. 9, the contact area 180 of the half-ellipsoidal head cap 100 is shown in contact with a glenoid of a shoulder. Due to the ellipsoidal shape, the surface of contact between the head cap and the glenoid—the glenoid contact surface 180—is larger as compared to devices of related art.

Figure 10:
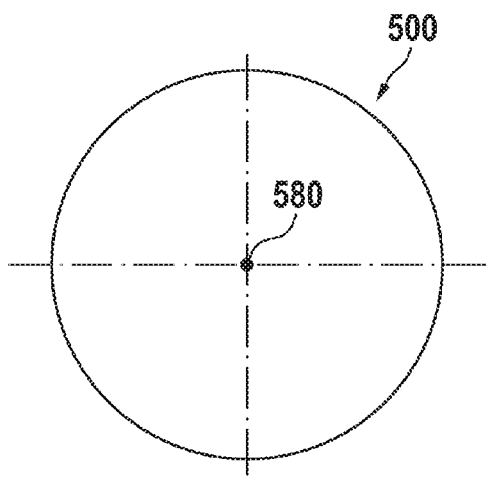
FIG. 10 shows the contact surface area of a spherical implant head.

In FIG. 10, the contact area 520 of an alternative spherically-shaped head cap 500 of a related embodiment of the implant is shown. Here, the contact area 520 has a circular shape and is significantly smaller than the contact area of an half-ellipsoidal head cap as shown before.

It will be appreciated to those skilled in the art having the benefit of this disclosure that implementations of this invention provide a humerus head prosthesis. Further modifications and alternative embodiments of various aspects of the invention will be apparent to those skilled in the art in view of this description. Accordingly, this description is to be construed as illustrative only and is provided for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 100 head cap
110 articulating surface
120 conical recess
121 recess radius
122 recess height
130 adapter contact surface
140 rim of adapter contact surface
142 extension surface
150 ellipsoid head z-axis
151 cap width
152 cap height
160 center of conical recess
161 outer radius of contact surface
180 glenoid contact area
200 fixing component
210 head adapter
211 protrusion
212 bore
213 chamfer
214 head contact surface
215 rim of head contact surface
216 conical section
220 bone-screw component
221 thread
222 centering shaft
223 limit stop
225 holes
226 cutting edges
300 humerus
310 humerus head
320 humerus center
500 spherical head cap
520 glenoid contact area of spherical head cap

The invention claimed is:
1. A humerus head implant comprising:
a head cap and a fixing component,
the head cap having a body enclosed between (i) an outer curved articulating surface that defines a half-ellipsoidal shape of the head cap and (ii) an inner surface that defines a conical recess in the body and that includes an extension surface surrounding said conical recess, wherein, when a local coordinate system is chosen such that a z-axis is transverse to and directed from the extension surface to the outer curved articulating surface and an x-axis and a y-axis are in a plane of the extension surface:
a) an intersection of the z-axis with the outer curved surface represents a center of the outer curved articulating surface that, in operation of the implant, is aligned along the z-axis with a first point chose to represent a center of humerus, and
b) a center axis of the conical recess is transverse to the extension surface and is displaced along the y-axis from the z-axis such that the body is asymmetric with respect to the z-axis
and
wherein a ratio of an x-extent of the head cap along the x-axis to a y-extent of the cap along the y-axis is in a range from 0.8 to 0.95,
the fixing component comprising:
a conical section dimensioned to fit into the conical recess and to allow for rotation of the head cap relative to the fixing component, and
a bone-screw component.

2. The humerus head implant according to claim 1, wherein the fixing component includes a head adapter containing said conical section and configured to form an interface between the bone-screw component and the head cap.

3. The humerus head implant according to claim 2, wherein the head adapter comprises at least one protrusion dimensioned to secure the head adapter against rotation.

4. The humerus head implant according to claim 1, wherein the ratio is between 0.85 and 0.95.

5. The humerus head implant according to claim 4, wherein the ratio is between 0.90 and 0.91.

6. The humerus head implant according to claim 1, wherein a displacement of the center axis along the y-axis with respect to the z-axis is between 3 and 10 mm such that, when the fixing component is operably cooperated with the head cap, an axis of the bone-screw component is spatially coordinated with a first spatial region separated from a second spatial region, chosen to represent a greater tubercle, by the first point to increase a degree of operational anchoring of the humerus head implant.

7. The humerus head implant according to claim 6, wherein the displacement is between 4 and 6 mm.

8. The humerus head implant according to claim 1, wherein the bone-screw component has a plurality of holes defined therethrough.

9. The humerus head implant according to claim 1, wherein the bone-screw-component has a limit stop ridge at an end thereof and an internal surface of the conical section contains a chamfer dimensioned to accommodate said limit stop ridge when the bone-screw component is disposed inside the conical section.

10. The humerus head implant according to claim 1, wherein the inner surface includes an adapter contact surface portion surrounding the conical recess and separated from the extension surface along the z-axis.

11. The humerus head implant according to claim 10, wherein the fixing component includes a head adapter containing said conical section and a head contact surface that surrounds the conical section and that is dimensioned to contact the adapter contact surface portion when the fixing component and the head cap are operably cooperated with one another.

* * * * *